United States Patent
Casement et al.

(10) Patent No.: US 9,770,218 B2
(45) Date of Patent: Sep. 26, 2017

(54) METHOD OF MAKING A RADIOGRAPHIC GUIDE AND A SURGICAL STENT/GUIDE FOR DENTAL IMPLANTS

(71) Applicant: Provisional Implant Technology LLC, Denver, CO (US)

(72) Inventors: Russell Casement, Parker, CO (US); Kelley Casement, Denver, CO (US); Ricardo Gapski, Parana (BR)

(73) Assignee: PROVISIONAL IMPLANT TECHNOLOGY, LLC, Denver, CO (US)

( * ) Notice: Subject to any disclaimer, the term of this patent is extended or adjusted under 35 U.S.C. 154(b) by 0 days.

(21) Appl. No.: 15/131,162

(22) Filed: Apr. 18, 2016

(65) Prior Publication Data

US 2016/0302743 A1    Oct. 20, 2016

Related U.S. Application Data

(60) Provisional application No. 62/150,058, filed on Apr. 20, 2015.

(51) Int. Cl.
  *A61B 6/14*    (2006.01)
  *A61C 1/08*    (2006.01)
  (Continued)

(52) U.S. Cl.
  CPC .............. *A61B 6/14* (2013.01); *A61B 6/12* (2013.01); *A61C 1/084* (2013.01); *A61C 9/00* (2013.01);
  (Continued)

(58) Field of Classification Search
  CPC .......... A61C 1/084; A61C 1/085; A61C 3/02; A61C 8/0089; A61C 9/00; A61C 13/34;
  (Continued)

(56) References Cited

U.S. PATENT DOCUMENTS 4,015,332 A    4/1977  Manne
4,203,515 A    5/1980  Kahn et al.
(Continued)

FOREIGN PATENT DOCUMENTS

EP        0803232        10/1997
WO    WO 02/069834        9/2002
(Continued)

OTHER PUBLICATIONS

International Search Report and Written Opinion for U.S. International (PCT) Patent Application No. PCT/US16/28331, dated Jul. 21, 2016, 10 pages.
(Continued)

*Primary Examiner* — Nicholas Lucchesi
(74) *Attorney, Agent, or Firm* — Lewis Brisbois Bisgaard & Smith LLP; Craig W. Mueller (57) ABSTRACT

A radiographic guide that can be used as a surgical guide is provided. The radiographic guide uses a provisional dental implant instead of a denture tooth or a custom made diagnostic tooth. The provisional dental implant, which can be integrated or selectively interconnected to the radiographic guide, may have a through-hole or a tapped hole that facilitates location of a dental implant. If the planned implant location is acceptable, the radiographic guide can be used as a surgical guide, wherein the hole guides surgical tools used to modify a patient's maxilla or jaw so it can receive the implant.

18 Claims, 5 Drawing Sheets

(51) Int. Cl.
*A61C 9/00* (2006.01)
*A61C 13/34* (2006.01)
*A61B 6/12* (2006.01)
A61C 8/00 (2006.01)
A61B 90/00 (2016.01)

(52) U.S. Cl.
CPC ...... *A61C 13/34* (2013.01); *A61B 2090/3966* (2016.02); *A61C 2008/0084* (2013.01)

(58) Field of Classification Search
CPC ..... A61C 2008/0084; A61B 6/14; A61B 6/12; A61B 2090/3966
See application file for complete search history.

(56) References Cited

U.S. PATENT DOCUMENTS

| | | | |
|---|---|---|---|
| 4,881,898 A * | 11/1989 | Harvey, Sr. | A61C 5/10 433/214 |
| 4,993,950 A | 2/1991 | Mensor, Jr. | |
| 5,006,069 A | 4/1991 | Lazzara et al. | |
| 5,040,983 A | 8/1991 | Binon | |
| 5,120,223 A | 6/1992 | Weissman | |
| 5,123,842 A | 6/1992 | Roberts | |
| 5,180,303 A | 1/1993 | Hornburg et al. | |
| D362,720 S | 9/1995 | Holmen et al. | |
| 5,458,489 A | 10/1995 | Tennyson | |
| 5,599,185 A | 2/1997 | Greenberg | |
| 5,779,480 A | 7/1998 | Groll et al. | |
| 5,785,526 A * | 7/1998 | Barnes | A61C 13/225 433/178 |
| 5,873,721 A * | 2/1999 | Willoughby | A61C 8/0001 433/172 |
| 5,951,294 A | 9/1999 | Pierson | |
| 5,967,777 A | 10/1999 | Klein et al. | |
| 6,024,567 A | 2/2000 | Callan | |
| 6,174,167 B1 | 1/2001 | Wohrle | |
| 6,190,171 B1 | 2/2001 | Hajjar et al. | |
| 6,431,867 B1 | 8/2002 | Gittelson et al. | |
| 6,663,387 B2 | 12/2003 | Riley | |
| D486,914 S | 2/2004 | Schulter et al. | |
| 6,746,244 B2 | 6/2004 | Riley et al. | |
| 6,884,073 B2 | 4/2005 | Chilibeck | |
| 6,887,077 B2 | 5/2005 | Porter et al. | |
| 6,935,862 B2 | 8/2005 | Harlan | |
| 7,097,451 B2 * | 8/2006 | Tang | A61B 17/176 433/76 |
| D567,947 S | 4/2008 | Lerner et al. | |
| D580,059 S | 11/2008 | Boettcher | |
| D587,371 S | 2/2009 | Purga et al. | |
| D587,373 S | 2/2009 | Purga et al. | |
| D659,829 S | 5/2012 | Nihei et al. | |
| D663,032 S | 7/2012 | Mashio et al. | |
| D663,419 S | 7/2012 | Mashio et al. | |
| D733,886 S | 7/2015 | Casement et al. | |
| D734,465 S | 7/2015 | Casement et al. | |
| D751,203 S | 3/2016 | Casement et al. | |
| D752,752 S | 3/2016 | Casement et al. | |
| 2002/0004189 A1 | 1/2002 | Hurson | |
| 2002/0039718 A1 | 4/2002 | Kwan | |
| 2002/0160337 A1 * | 10/2002 | Klein | A61C 1/084 433/213 |
| 2003/0044749 A1 * | 3/2003 | Marotta | A61C 1/084 433/45 |
| 2004/0219479 A1 | 11/2004 | Malin et al. | |
| 2005/0084144 A1 | 4/2005 | Feldman | |
| 2005/0084821 A1 | 4/2005 | Sims et al. | |
| 2006/0183078 A1 | 8/2006 | Niznick | |
| 2006/0188844 A1 | 8/2006 | Dadi | |
| 2007/0031793 A1 | 2/2007 | Casement et al. | |
| 2008/0020343 A1 | 1/2008 | Mount | |
| 2008/0176187 A1 | 7/2008 | Stempel | |
| 2008/0261177 A1 | 10/2008 | Ford et al. | |
| 2009/0017421 A1 * | 1/2009 | Letcher | A61C 13/0003 433/201.1 |
| 2010/0227294 A1 | 9/2010 | Takagi et al. | |
| 2012/0135373 A1 | 5/2012 | Cheng et al. | |
| 2013/0171587 A1 | 7/2013 | Akutsu | |
| 2014/0026419 A1 | 1/2014 | Haber | |
| 2014/0193771 A1 | 7/2014 | Dolfi et al. | |
| 2015/0351866 A1 * | 12/2015 | Thompson, Jr. | A61C 1/084 433/173 |

FOREIGN PATENT DOCUMENTS

| | | |
|---|---|---|
| WO | WO 2009/001007 | 12/2008 |
| WO | DM 077057 | 9/2011 |
| WO | WO 2013/186702 | 12/2013 |

OTHER PUBLICATIONS

"Nobel Clinician—Quick Guide," Haupt Dental Lab Inc., 2012, 5 pages.

"Radiographic Guide Protocol," iDent Imaging Inc., 2009, retrieved from http://ident-surgical.com/wp-content/uploads/Scan%20Device%20Protocol%20v4.2.pdf, retrieved on Aug. 3, 2016, 3 pages.

"Radiographic/Surgical Guides," Periodontics and Oral Medicine, 2014, retrieved from http://www.njperioimplant.com/referring-doctors/radiographicssurgical-guides, retrieved on Sep. 16, 2014, 6 pages.

"SICAT Surgical Guides," SICAT GmbH & Co. KG, 2012, 53 pages.

Amresco, Inc, Product Detail Acryl/Bis 19:1., 2 pages.

Amresco, Inc, Product Detail Acrylamide, 3 pages.

Craig, "Dental Materials Properties and Manipulation," 8th edition, Mosby Inc., 2004, 117 pages.

Dentsply Ceramco, Firing Guidelines for Ceramco Products. © Mar. 2006, 7 pages.

Dynalab Group, Plastic Properties of Polymethylmethacrylate (Acrylic), retrieved on Oct. 22, 2007, 2 pages.

GE Plastics, DataSheets Lexan Resins, All Series, 2 pages.

Greenstein, "The Relationship Between Biologic Concepts and Fabrication fo Surgical guides for Dental Implant Placement," Compendium, 2007, 28(4), pp. 130-137.

McCabe, "Applied Dental Materials," 8th Edition, Blackwell Science Ltd., 1998, 20 pages.

Montrose, "Fabrication of a Surgical Implant Template With Guide Tubes," Dentistry Today, 2003, retrieved from http://www.dentistrytoday.com/ce-articles/383, retrieved on Sep. 16, 2014, 7 pages.

O'Brien, WJ, Dental Materials and Their Selection, 2nd Edition, © 1997, Quintessence Publishing Co, Inc., pp. 51-77, 123-146, 147-150, 151-174, 215-223.

Orentlicher, "Computer-Guided Planning and Placement of Dental Implants," Atlas of the Oral and Maxillofacial Surg Clin N Am, 2012, vol. 20, pp. 53-79.

Powers, "Craig's Restorative Dental Materials," 12th Edition, Elsevier, Inc., 2006, 41 pages.

Ramasamy, "Implant surgical guides: From the past to the present," Journal of Pharmacy and Bioallied Sciences, 2013, vol. 5(supp. 1); 8 pages.

San Diego Plastics, Inc, Polycarbonate (Makrolon®, Lexan®, Zelux®), 4 pages.

Official Action for U.S. Appl. No. 11/401,763 dated Sep. 16, 2008, 16 pages.

Official Action for U.S. Appl. No. 11/401,763 dated Mar. 27, 2009, 10 pages.

Official Action for U.S. Appl. No. 11/401,763 dated Sep. 14, 2009, 8 pages.

Official Action for U.S. Appl. No. 11/401,763 dated May 18, 2010, 8 pages.

Official Action for U.S. Appl. No. 11/401,763 dated Oct. 4, 2011, 12 pages.

Official Action for U.S. Appl. No. 11/197,743 dated Jul. 5, 2006, 8 pages.

Official Action for U.S. Appl. No. 11/197,743 dated Dec. 21, 2006, 8 pages.

(56) References Cited

OTHER PUBLICATIONS

Official Action for U.S. Appl. No. 11/197,743 dated May 4, 2007, 6 pages.
Official Action for U.S. Appl. No. 11/197,743 dated Aug. 31, 2007, 7 pages.
Official Action for U.S. Appl. No. 11/197,743 dated Jan. 23, 2008, 8 pages.
Official Action for U.S. Appl. No. 11/197,743 dated May 22, 2008, 9 pages.
Official Action for U.S. Appl. No. 11/197,743 dated Feb. 27, 2009, 8 pages.
Official Action for U.S. Appl. No. 11/197,743 dated Sep. 9, 2009, 8 pages.
Official Action for U.S. Appl. No. 11/197,743 dated Jun. 18, 2010, 9 pages.
Official Action for U.S. Appl. No. 11/197,743 dated Aug. 15, 2012, 11 pages.
Official Action for U.S. Appl. No. 11/197,743 dated Jul. 30, 2013, 12 pages.
Official Action for U.S. Appl. No. 11/197,743 dated Feb. 11, 2014, 9 pages.
Notice of Allowance for U.S. Appl. No. 29/471,531 dated May 20, 2015, 9 pages.
Official Action for U.S. Appl. No. 29/529,316 dated Oct. 7, 2015, 6 pages.
Notice of Allowance for U.S. Appl. No. 29/529,316 dated Nov. 18, 2015, 7 pages.
Notice of Allowance for U.S. Appl. No. 29/471,534 dated May 7, 2015, 10 pages.
Official Action for U.S. Appl. No. 29/529,318 dated Oct. 7, 2015, 6 pages.
Notice of Allowance for U.S. Appl. No. 29/529,318 dated Nov. 18, 2015, 7 pages.

\* cited by examiner

FIG.7

METHOD OF MAKING A RADIOGRAPHIC GUIDE AND A SURGICAL STENT/GUIDE FOR DENTAL IMPLANTS

This application claims the benefit of U.S. Provisional Patent Application Ser. No. 62/150,058, filed Apr. 20, 2015, the entirety of which is incorporated by reference herein.

This application is related to U.S. patent application Ser. No. 11/197,743, filed Aug. 3, 2005, which is incorporated by reference herein.

FIELD OF THE INVENTION

Embodiments of the present invention are generally related to radiographic and surgical guides used to identify an ideal location for a dental implant. In one embodiment, a provisional implant crown is used to fabricate the radiographic guide. In another embodiment, a provisional crown is used to fabricate a surgical stent for implant placement. In another embodiment, a provisional crown is used to facilitate the location of implant placement.

BACKGROUND OF THE INVENTION

Temporary and permanent crowns are anchored to a patient's maxilla or jaw by way of dental implant. The current method of placing a dental implant is time consuming, complex, and expensive. More specifically, current implant installation begins with planning from the implant location up to the desired crown location. That is, the dentist or oral surgeon first installs the implant at the tooth extraction site; ideally where ideal bone mass is present. After the implant is installed, an abutment, which connects the crown to the implant, and the crown are added to the implant. Often, the abutment and/or crown may have to be modified to be interconnected to the implant, because the best implant location with respect to the desired crown location is not feasible due to bone availability, implant angulation, and/or issues associated with alignment with, or placement next to, adjacent teeth.

The first step in identifying the ideal implant location is accomplished by assessing bone quantity, density, etc., which is done by obtaining radiographic measurements of the patient's mouth. To ensure the radiographic images correctly characterize the patient's physiology, a radiographic guide must be made. A common process of radiographic guide fabrication is generally comprised of first forming a cast of the patient's dental arch that includes at least one void (e.g., area associated with the extracted tooth or teeth) that is to be filled with a dental implant and permanent crown. A denture tooth is adjusted to fit the space and wax, or other adhering substance, is subsequently used to secure the denture tooth within the void of the dental cast. Alternatively, a custom made diagnostic tooth fills the void of the cast.

One such method involves using putty to make an impression of the denture tooth or custom made diagnostic tooth and the surrounding portions of the dental arch cast. The putty is then removed to reveal an impression of the denture tooth or custom made diagnostic tooth. The putty is trimmed to remove the impressions of the surrounding teeth. The denture tooth or custom made diagnostic tooth is then removed from the cast. A separating agent is then applied to the dental cast, and the putty impression of the denture tooth or custom made diagnostic tooth is filled with orthodontic resin (acrylic) to form a replica of the original denture tooth or custom made diagnostic tooth. The putty impression with the orthodontic resin is placed over the void and allowed to cure. The cured acrylic tooth that represents the lost tooth is removed from the putty impression and the dental arch cast and trimmed to remove excess resin.

Next, undercuts in the dental arch cast are filled with wax and the trimmed acrylic tooth that represents the lost tooth is placed back into the previously-formed putty impression. In addition, an orthodontic acrylic resin is mixed and a monomer is added to the fabricated acrylic tooth. The acrylic tooth, which is still in the putty, is placed back on the dental arch cast at the void site. The previously mixed orthodontic acrylic resin, which is still yet to be fully cured, is placed over the dental arch cast. The partially-cured orthodontic acrylic resin is molded over the "roof" (assuming a tooth associated with the patient's maxilla requires replacement) of the dental cast and the cast teeth adjacent to the putty-encapsulated acrylic tooth, thereby bonding the acrylic tooth to the orthodontic acrylic resin. Excess resin is trimmed and removed from the portion of the "roof" and from portions of the dental arch cast outer surface. The combination of orthodontic acrylic resin, putty, acrylic tooth, and dental arch cast is secured and the orthodontic acrylic resin is allowed to cure.

After the orthodontic acrylic resin is cured, the putty is removed and the acrylic tooth remains associated with the cured resin. The radiographic guide comprises the cured orthodontic acrylic resin removed from the dental arch cast. That is, the radiographic guide comprises an impression of the existing teeth with an interconnected acrylic tooth. Gutta percha markers or other radio-opaque markers, which are familiar to those of ordinary skill in the art, are then added to the radiographic guide. The radiographic guide is placed in the patient's mouth wherein the representation of the denture tooth or custom made diagnostic tooth is placed in the void associated with the lost tooth, and various radiographic images of the patient's mouth are obtained.

A surgical guide, which may be a copy of the radiographic guide, is then fabricated. Information gleaned from the radiographic images helps to define holes in the surgical guide that help the oral surgeon locate and drill a dental implant into the patient's mouth. Again, as one of ordinary skill the art will appreciate, this process is time consuming and complex.

Thus it is a long felt need in the field of dentistry and oral surgery to provide a more efficient and cost-effective way to create a radiographic and surgical guide. The following disclosure describes an improved method of fabricating a radiographic guide that can also be used as a surgical guide. The contemplated radiographic guide includes a provisional implant crown, or an impression of a provisional implant crown closely matched to a provisional implant crown that will be interconnected to an implant abutment after the implant surgery is completed.

SUMMARY OF THE INVENTION

It is one aspect of embodiments of the present invention to provide a method of locating a dental implant using a "top-down" approach. As outlined above, dental implants are currently placed in a patient's mouth at an ideal location with respect to bone mass, without concern for abutment location and the ultimate location of the provisional crown that will be interconnected to the implant. Thus the abutment and crown often need to be modified to be interconnected to the implant, and to accommodate the adjacent teeth, which is a complex and labor intensive process. Newer technologies, such as bone grafts, tissue grafts, implant coatings, abutment designs, etc., allow implant placement to be planned "crown-down." That is, the oral surgeon places the implant at a location that coincides with an ideal crown position, so long as sufficient bone mass is available or can be grafted at the implant site. This aspect of embodiments of the present invention can be achieved by the processes described herein.

More specifically, embodiments of the present invention are directed to a method of fabricating a radiographic guide that is 1) less labor intensive and complex than the prior art process; 2) does not use a denture tooth or custom made diagnostic tooth and the associated putty described above; and 3) is based on the shape of a provisional dental implant crown. Radiographic guides of one embodiment of the present invention are made by first fabricating a dental arch cast using prior art methods. Wax is then used to secure a provisional dental implant crown, which is not a denture tooth or custom made diagnostic tooth, to the dental arch at the site of the lost tooth or teeth. The provisional dental implant crown may be similar to those described in applicant's U.S. Patent Application Publication No. 20070031792, U.S. Patent Application Publication No. 20070031793, and U.S. Pat. Nos. D733,886, D751,203, D734,465, and D752,752, which are incorporated by reference herein. The provisional dental implant crown may have a symmetrical profile with a hole therethrough. Alternatively, a cavity extending from a lower surface of the provisional dental implant crown upwardly to a point below an upper surface of the provisional dental crown, i.e., a tapped hole, may be provided. The provisional crown may also be transparent or semi-transparent to allow the clinician to see through the crown while placing the implant. Next, undercuts in the dental arch cast are filled with wax as in the prior art method. Partially-cured orthodontic acrylic resin is placed over the dental arch cast and the provisional dental implant crown, and any excess orthodontic acrylic resin is trimmed. The radiographic guide, which comprises an impression of existing teeth made of cured orthodontic acrylic resin and an integrated provisional dental implant crown, is removed from the dental arch cast. Gutta percha markers, or other radio-opaque markers, are then added to the radiographic guide. In addition, a radio-opaque material (ex. gutta percha, barium sulfate, etc.) is used to coat the wall of the hole or tapped hole of the provisional implant crown. The radiographic guide is then placed in the patient's mouth wherein the provisional implant crown is located in the void defined by the lost tooth. Radiographic images of the patient's mouth are then obtained.

In the radiographic images, the hole or tapped hole of the provisional crown, previously filled with the radio-opaque material, will directly correspond to the straight line axis of the implant body to be placed. Information from the imaging also provides the angulation of the implant body that is to be attached to the patient's maxilla or jaw, and spatial relationship of the implant body, abutment and provisional crown positions before surgery commences.

The radiographic guide of one embodiment can also be used as a surgical guide, which will replace the need to make a separate surgical guide. That is, if the radiographic images show the bone density and bone quantity is acceptable, the hole provided by the radiographic guide can be used as a drilling template. If, however, the planned implant location associated with the hole is not ideal, the oral surgeon may create a new surgical guide from the radiographic guide, which may comprise repeating the radiographic guide fabrication process described above or utilizing a computer software CAD/CAM program to fabricate the surgical guide. For example, a different or modified provisional dental implant crown may be used to create a new radiographic guide.

After drilling is complete and the implant and abutment are placed in the patient's mouth, a provisional dental implant crown that matches that integrated into the radiographic guide is placed. Because the provisional dental implant crown matches the dimensions of the radiographic guide, it should fit perfectly in the patient's mouth and interconnect to the abutment.

The denture tooth or custom made diagnostic tooth used in the prior art methods does not include a prefabricated, precisely located hole that is of a predetermined tolerance. The dentist or surgeon must modify the denture tooth or custom made diagnostic tooth to create a hole, which will rarely coincide exactly with the axis of the yet-to-be secured implant or abutment. It follows that surgical guides made with modified denture teeth or custom made diagnostic teeth will not be precise. A misaligned hole in the denture tooth or custom diagnostic tooth will likely not fit correctly with the patient's anatomical topography and more specifically in respect to the surrounding teeth or bone where the implant will be placed. Consequently, when the denture tooth or custom made diagnostic tooth is interconnected to the implant via an abutment, it will have to be modified to be accepted by the abutment and dental implant. A provisional crown made from a denture tooth or custom made diagnostic tooth will not fit the base of the abutment nor will the provisional crown be of the correct vertical dimension, so it will require several modifications to be used as a provisional crown. It is also possible that it cannot be accepted by the implant or abutment and another crown must be custom made to be used as a temporary crown. To address this issue of misaligned implants, angled or non-standard abutments must be employed, and/or the provisional crown must be modified or remade—factors that increase patient "chair time" and cost. Alternatively, oral surgeons must use a software program that allows them to digitally "place an implant" and then have a surgical guide fabricated via CAD/CAM methods. Because digitally placing an implant includes a degree of guess work and "feel," this method suffers some of the same drawbacks experienced with using modified denture teeth or custom made diagnostic teeth.

One of ordinary skill in the art will appreciate that the contemplated hole in the provisional crown provides information during radiographic studies and during surgery for the surgical stent/guide. The prefabricated hole in the provisional crown allows a dentist or surgeon to accurately assess the future implant's placement and angulation during the radiographic studies, because the orientation of the future implant will coincide with the provisional crown's hole axis. The axis of the provisional crown may also coincide with the axis of the abutment.

The following table provides a comparison of the traditional method described above to embodiments of the present invention.

| Feature | Traditional method | Embodiments of the present invention |
|---|---|---|
| Initial impression of the patient's mouth | Required | Required |
| Fabricating a dental cast from the impression | Required | Required |
| Type of "tooth" incorporated into the gaps of the missing teeth | Denture tooth or custom | Provisional crown |

-continued

| Feature | Traditional method | Embodiments of the present invention |
|---|---|---|
| | diagnostic waxed tooth | |
| Take an impression of the dental cast containing the denture tooth | Required | Not required |
| Fabricating a replica tooth in orthodontic resin from the impression | Required | Not required |
| Application of partially-cured orthodontic acrylic resin, or other material as is known in the art, over the cast and replacement tooth | Required | Required |
| Fabricate a hole through the tooth along the anticipated implant axis | Required | Not required |
| Application of radio-opaque material to the guide | Required | Required |
| Fabrication of a new surgical guide | Required | Not required - can be converted from the radiographic guide |

It is one aspect of embodiments of the present invention to provide a method of fabricating a radiographic guide, comprising: taking an impression of a patient's dental arch; using the impression to create a cast of a patient's dental arch, the cast including at least one void; using wax to interconnect a provisional implant crown to the cast, the provisional implant crown being associated with the at least one void; applying partially-cured orthodontic acrylic resin over the cast and the provisional implant crown; allowing the orthodontic acrylic resin to cure, which causes the provisional implant crown to bond with the orthodontic acrylic resin; and removing the cured orthodontic acrylic resin and interconnected provisional implant crown from the cast.

It is another aspect of embodiments of the present invention to provide a method of fabricating a radiographic guide that can be used as a surgical guide, comprising: obtaining an impression of a patient's dental arch; using the impression to create a cast of a patient's dental arch, the cast including at least one void; associating at least one tooth representation with the at least one void, the at least one tooth representation having a hole; applying orthodontic acrylic resin over the cast and the at least one tooth representation; curing the orthodontic acrylic resin; and removing the cured orthodontic acrylic resin and the at least one tooth representation from the cast.

It is yet another aspect of embodiments of the present invention to provide a radiographic guide, comprising: a shaped member having a plurality of recesses adapted for receipt of patient's teeth, the shaped member having an outer profile that generally corresponds to the shape of at least one of the patient's teeth; a provisional dental implant crown positioned in one of the plurality of recesses, the provisional dental implant comprises a hole.

It is another aspect of embodiments of the present invention to provide a method of placing a provisional implant crown into a patient's maxilla or jaw, comprising: obtaining an impression of a patient's dental arch; using the impression to create a cast of a patient's dental arch, the cast including a void that corresponds with an extracted tooth; associating a tooth representation with void, the tooth representation having a hole; applying orthodontic acrylic resin over the cast and the tooth representation; curing the orthodontic acrylic resin; removing the cured orthodontic acrylic resin and the at least one tooth representation from the cast; placing the radiographic guide into the patient's mouth wherein the tooth representation is associated with the site of the extracted tooth; obtaining a radiographic image of the radiographic guide; analyzing the image to assess if the hole is positioned and aligned with an area of the patient's maxilla or jaw that is conducive for accepting and securing a dental implant; using the radiographic guide as a surgical guide, wherein the hole is used to guide surgical tools that prepare the patient's maxilla or jaw for receipt of an implant; interconnecting the implant to the patient's maxilla or jaw; interconnecting an abutment to the implant; and interconnecting the provisional implant crown to the abutment.

Further aspects of the present invention are provided in the following embodiments:

A method of fabricating a radiographic guide, comprising: taking an impression of a patient's dental arch; using the impression to create a cast of a patient's dental arch, the cast including at least one void; using wax to interconnect a provisional implant crown to the cast, the provisional implant crown being associated with the at least one void; applying partially-cured orthodontic acrylic resin over the cast and the provisional implant crown; allowing the orthodontic acrylic resin to cure, which causes the provisional implant crown to bond with the orthodontic acrylic resin; and removing the cured orthodontic acrylic resin and interconnected provisional implant crown from the cast, wherein the provisional implant crown includes a hole therethrough.

A method of fabricating a radiographic guide, comprising: taking an impression of a patient's dental arch; using the impression to create a cast of a patient's dental arch, the cast including at least one void; using wax to interconnect a provisional implant crown to the cast, the provisional implant crown being associated with the at least one void; applying partially-cured orthodontic acrylic resin over the cast and the provisional implant crown; allowing the orthodontic acrylic resin to cure, which causes the provisional implant crown to bond with the orthodontic acrylic resin; and removing the cured orthodontic acrylic resin and interconnected provisional implant crown from the cast, wherein the provisional implant crown includes a hole therethrough, further comprising at least one of coating a surface of the hole with a radio-opaque material, and adding radiographic markers to the radiographic guide.

A method of fabricating a radiographic guide, comprising: taking an impression of a patient's dental arch; using the impression to create a cast of a patient's dental arch, the cast including at least one void; using wax to interconnect a provisional implant crown to the cast, the provisional implant crown being associated with the at least one void; applying partially-cured orthodontic acrylic resin over the cast and the provisional implant crown; allowing the orthodontic acrylic resin to cure, which causes the provisional implant crown to bond with the orthodontic acrylic resin; and removing the cured orthodontic acrylic resin and interconnected provisional implant crown from the cast, further comprising adding a separating agent to the cast, but not the provisional implant crown.

A method of fabricating a radiographic guide, comprising: taking an impression of a patient's dental arch; using the impression to create a cast of a patient's dental arch, the cast including at least one void; using wax to interconnect a provisional implant crown to the cast, the provisional implant crown being associated with the at least one void; applying partially-cured orthodontic acrylic resin over the cast and the provisional implant crown; allowing the orthodontic acrylic resin to cure, which causes the provisional implant crown to bond with the orthodontic acrylic resin;

and removing the cured orthodontic acrylic resin and interconnected provisional implant crown from the cast, further comprising obtaining a radiographic image of the radiographic guide positioned in the patient's mouth, and analyzing the image to assess if the hole is positioned and aligned with an area of the patient's maxilla or jaw that is conducive for accepting and securing a dental implant.

A method of fabricating a radiographic guide, comprising: taking an impression of a patient's dental arch; using the impression to create a cast of a patient's dental arch, the cast including at least one void; using wax to interconnect a provisional implant crown to the cast, the provisional implant crown being associated with the at least one void; applying partially-cured orthodontic acrylic resin over the cast and the provisional implant crown; allowing the orthodontic acrylic resin to cure, which causes the provisional implant crown to bond with the orthodontic acrylic resin; and removing the cured orthodontic acrylic resin and interconnected provisional implant crown from the cast, further comprising obtaining a radiographic image of the radiographic guide positioned in the patient's mouth, and analyzing the image to assess if the hole is positioned and aligned with an area of the patient's maxilla or jaw that is conducive for accepting and securing a dental implant, further comprising removing the radiographic guide from the patient's mouth, removing the radio-opaque material from the hole, creating a new hole in the provisional implant crown, and coating the new hole with a radio-opaque material, placing the radiographic guide into the patient's mouth, and obtaining a second radiographic image, and analyzing the second image to assess if the new hole is positioned and aligned with the area of the patient's maxilla or jaw that is conducive for accepting and securing a dental implant.

A method of fabricating a radiographic guide that can be used as a surgical guide, comprising: obtaining an impression of a patient's dental arch; using the impression to create a cast of a patient's dental arch, the cast including at least one void; associating at least one tooth representation with the at least one void, the at least one tooth representation having a hole; applying orthodontic acrylic resin over the cast and the at least one tooth representation; curing the orthodontic acrylic resin; and removing the cured orthodontic acrylic resin and the at least one tooth representation from the cast, wherein the at least one tooth representation is a provisional implant crown that substantially matches the shape of a provisional implant crown that will be interconnected to a dental implant via an abutment.

A method of fabricating a radiographic guide that can be used as a surgical guide, comprising: obtaining an impression of a patient's dental arch; using the impression to create a cast of a patient's dental arch, the cast including at least one void; associating at least one tooth representation with the at least one void, the at least one tooth representation having a hole; applying orthodontic acrylic resin over the cast and the at least one tooth representation; curing the orthodontic acrylic resin; and removing the cured orthodontic acrylic resin and the at least one tooth representation from the cast, wherein the at least one tooth representation is bonded to the cured orthodontic resin.

A method of fabricating a radiographic guide that can be used as a surgical guide, comprising: obtaining an impression of a patient's dental arch; using the impression to create a cast of a patient's dental arch, the cast including at least one void; associating at least one tooth representation with the at least one void, the at least one tooth representation having a hole; applying orthodontic acrylic resin over the cast and the at least one tooth representation; curing the orthodontic acrylic resin; and removing the cured orthodontic acrylic resin and the at least one tooth representation from the cast, wherein the at least one tooth representation is selectively interconnected to the cured orthodontic resin.

A method of fabricating a radiographic guide that can be used as a surgical guide, comprising: obtaining an impression of a patient's dental arch; using the impression to create a cast of a patient's dental arch, the cast including at least one void; associating at least one tooth representation with the at least one void, the at least one tooth representation having a hole; applying orthodontic acrylic resin over the cast and the at least one tooth representation; curing the orthodontic acrylic resin; and removing the cured orthodontic acrylic resin and the at least one tooth representation from the cast, wherein the hole does not extend through the at least one tooth representation.

A method of fabricating a radiographic guide that can be used as a surgical guide, comprising: obtaining an impression of a patient's dental arch; using the impression to create a cast of a patient's dental arch, the cast including at least one void; associating at least one tooth representation with the at least one void, the at least one tooth representation having a hole; applying orthodontic acrylic resin over the cast and the at least one tooth representation; curing the orthodontic acrylic resin; and removing the cured orthodontic acrylic resin and the at least one tooth representation from the cast, further comprising at least one of coating the hole with a radio-opaque material, and adding radiographic markers to the radiographic guide.

A method of fabricating a radiographic guide that can be used as a surgical guide, comprising: obtaining an impression of a patient's dental arch; using the impression to create a cast of a patient's dental arch, the cast including at least one void; associating at least one tooth representation with the at least one void, the at least one tooth representation having a hole; applying orthodontic acrylic resin over the cast and the at least one tooth representation; curing the orthodontic acrylic resin; and removing the cured orthodontic acrylic resin and the at least one tooth representation from the cast, further comprising obtaining a radiographic image of the radiographic guide positioned in the patient's mouth, and analyzing the image to assess if the hole is positioned and aligned with an area of the patient's maxilla or jaw that is conducive for accepting and securing a dental implant.

A method of fabricating a radiographic guide that can be used as a surgical guide, comprising: obtaining an impression of a patient's dental arch; using the impression to create a cast of a patient's dental arch, the cast including at least one void; associating at least one tooth representation with the at least one void, the at least one tooth representation having a hole; applying orthodontic acrylic resin over the cast and the at least one tooth representation; curing the orthodontic acrylic resin; and removing the cured orthodontic acrylic resin and the at least one tooth representation from the cast, further comprising obtaining a radiographic image of the radiographic guide positioned in the patient's mouth, and analyzing the image to assess if the hole is positioned and aligned with an area of the patient's maxilla or jaw that is conducive for accepting and securing a dental implant, further comprising removing the radiographic guide from the patient's mouth, removing the radio-opaque material from the hole, creating a new hole in the provisional implant crown, and coating the new hole with a radio-opaque material, placing the radiographic guide into the patient's mouth, and obtaining a second radiographic image of the radiographic guide, and analyzing the second image to assess if the new hole is positioned and aligned with the area of the patient's maxilla or jaw that is conducive for accepting and securing a dental implant.

A radiographic guide, comprising: a shaped member having a plurality of recesses adapted for receipt of patient's teeth, the shaped member having an outer profile that generally corresponds to the shape of at least one of the patient's teeth; a provisional dental implant crown positioned in one of the plurality of recesses, the provisional dental implant comprises a hole, wherein the provisional dental implant does not correspond to the outer shape of the patient's extracted tooth.

A radiographic guide, comprising: a shaped member having a plurality of recesses adapted for receipt of patient's teeth, the shaped member having an outer profile that generally corresponds to the shape of at least one of the patient's teeth; a provisional dental implant crown positioned in one of the plurality of recesses, the provisional dental implant comprises a hole, wherein the shaped member is made of acrylic that includes radio-opaque areas.

A radiographic guide, comprising: a shaped member having a plurality of recesses adapted for receipt of patient's teeth, the shaped member having an outer profile that generally corresponds to the shape of at least one of the patient's teeth; a provisional dental implant crown positioned in one of the plurality of recesses, the provisional dental implant comprises a hole, wherein the provisional dental implant crown is selectively interconnected to the shaped member.

A method of placing a provisional implant crown into a patient's maxilla or jaw, comprising: obtaining an impression of a patient's dental arch; using the impression to create a cast of a patient's dental arch, the cast including a void that corresponds with an extracted tooth; associating a tooth representation with void, the tooth representation having a hole; applying orthodontic acrylic resin over the cast and the tooth representation; curing the orthodontic acrylic resin; removing the cured orthodontic acrylic resin and the at least one tooth representation from the cast; placing the radiographic guide into the patient's mouth wherein the tooth representation is associated with the site of the extracted tooth; obtaining a radiographic image of the radiographic guide; analyzing the image to assess if the hole is positioned and aligned with an area of the patient's maxilla or jaw that is conducive for accepting and securing a dental implant; using the radiographic guide as a surgical guide, wherein the hole is used to guide surgical tools that prepare the patient's maxilla or jaw for receipt of an implant; interconnecting the implant to the patient's maxilla or jaw; interconnecting an abutment to the implant; and interconnecting the provisional implant crown to the abutment, wherein the tooth representation has a shape substantially similar to that of the provisional implant crown.

A method of placing a provisional implant crown into a patient's maxilla or jaw, comprising: obtaining an impression of a patient's dental arch; using the impression to create a cast of a patient's dental arch, the cast including a void that corresponds with an extracted tooth; associating a tooth representation with void, the tooth representation having a hole; applying orthodontic acrylic resin over the cast and the tooth representation; curing the orthodontic acrylic resin; removing the cured orthodontic acrylic resin and the at least one tooth representation from the cast; placing the radiographic guide into the patient's mouth wherein the tooth representation is associated with the site of the extracted tooth; obtaining a radiographic image of the radiographic guide; analyzing the image to assess if the hole is positioned and aligned with an area of the patient's maxilla or jaw that is conducive for accepting and securing a dental implant; using the radiographic guide as a surgical guide, wherein the hole is used to guide surgical tools that prepare the patient's maxilla or jaw for receipt of an implant; interconnecting the implant to the patient's maxilla or jaw; interconnecting an abutment to the implant; and interconnecting the provisional implant crown to the abutment, wherein if after analyzing, the proposed implant placement is not ideal, removing the radiographic guide from the patient's mouth, removing the radio-opaque material from the hole, creating a new hole in the provisional implant crown, and coating the new hole with a radio-opaque material, placing the radiographic guide into the patient's mouth, and obtaining a second radiographic image of the radiographic guide, and analyzing the second image to assess if the new hole is positioned and aligned with the area of the patient's maxilla or jaw that is conducive for accepting and securing a dental implant.

A method of placing a provisional implant crown into a patient's maxilla or jaw, comprising: obtaining an impression of a patient's dental arch; using the impression to create a cast of a patient's dental arch, the cast including a void that corresponds with an extracted tooth; associating a tooth representation with void, the tooth representation having a hole; applying orthodontic acrylic resin over the cast and the tooth representation; curing the orthodontic acrylic resin; removing the cured orthodontic acrylic resin and the at least one tooth representation from the cast; placing the radiographic guide into the patient's mouth wherein the tooth representation is associated with the site of the extracted tooth; obtaining a radiographic image of the radiographic guide; analyzing the image to assess if the hole is positioned and aligned with an area of the patient's maxilla or jaw that is conducive for accepting and securing a dental implant; using the radiographic guide as a surgical guide, wherein the hole is used to guide surgical tools that prepare the patient's maxilla or jaw for receipt of an implant; interconnecting the implant to the patient's maxilla or jaw; interconnecting an abutment to the implant; and interconnecting the provisional implant crown to the abutment, further comprising at least one of coating the hole with a radio-opaque material, and adding radiographic markers to the radiographic guide.

These and other advantages will be apparent from the disclosure of the invention(s) contained herein. The above-described embodiments, objectives, and configurations are neither complete nor exhaustive. As will be appreciated, other embodiments of the invention are possible using, alone or in combination, one or more of the features set forth above or described below. Further, the Summary of the Invention is neither intended nor should it be construed as being representative of the full extent and scope of the present invention. Moreover, references made herein to "the present invention" or aspects thereof should be understood to mean certain embodiments of the present invention and should not necessarily be construed as limiting all embodiments to a particular description. The present invention is set forth in various levels of detail in the Summary of the Invention as well as in the attached drawings and the Detailed Description of the Invention and no limitation as to the scope of the present invention is intended by either the inclusion or non-inclusion of elements, components, etc. in this Summary of the Invention. Additional aspects of the present invention will become more readily apparent from the Detail Description, particularly when taken together with the drawings.

BRIEF DESCRIPTION OF THE DRAWINGS

The accompanying drawings, which are incorporated in and constitute a part of the specification, illustrate embodiments of the invention and together with the general description of the invention given above and the detailed description of the drawings given below, serve to explain the principles of these inventions.

To assist in the understanding of one embodiment of the present invention the following list of components and associated numbering found in the drawings is provided herein:

| # | Component |
|---|---|
| 2 | Provisional dental crown |
| 6 | Outer surface |
| 10 | Conical portion |
| 14 | Hole |
| 18 | Radiographic guide |
| 22 | Dental arch cost |
| 26 | Tooth representation |
| 30 | Void |
| 34 | Wax |
| 38 | Orthodontic acrylic resin |
| 40 | Recess |
| 42 | Marker |
| 46 | Radio-opaque material |

It should be understood that the drawings are not necessarily to scale. In certain instances, details that are not necessary for an understanding of the invention or that render other details difficult to perceive may have been omitted. It should be understood, of course, that the invention is not necessarily limited to the particular embodiments illustrated herein.

DETAILED DESCRIPTION

Figure 1:
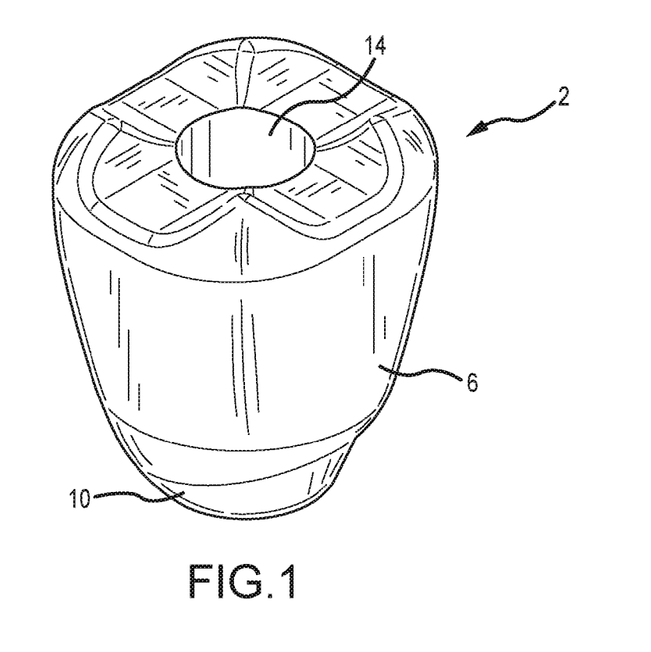
FIG. 1 is a provisional dental crown used in one embodiment of the present invention.
Figure 2:
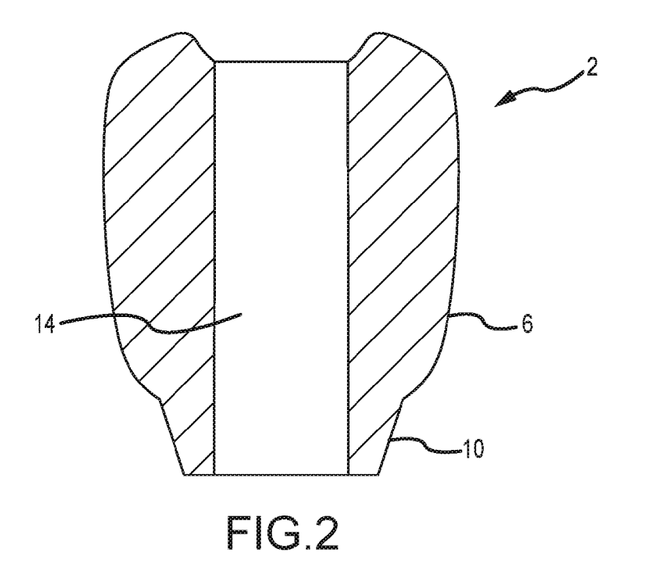
FIG. 2 is a cross-sectional view of FIG. 1.
Figure 3:
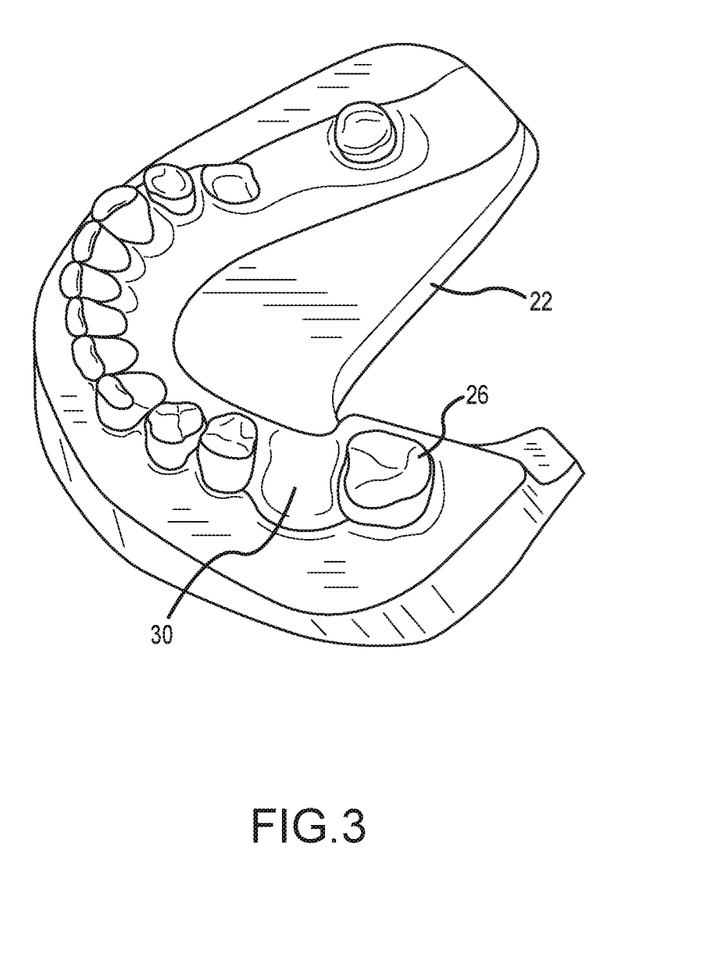
FIG. 3 is a perspective view of a dental arch cast.
Figure 4:
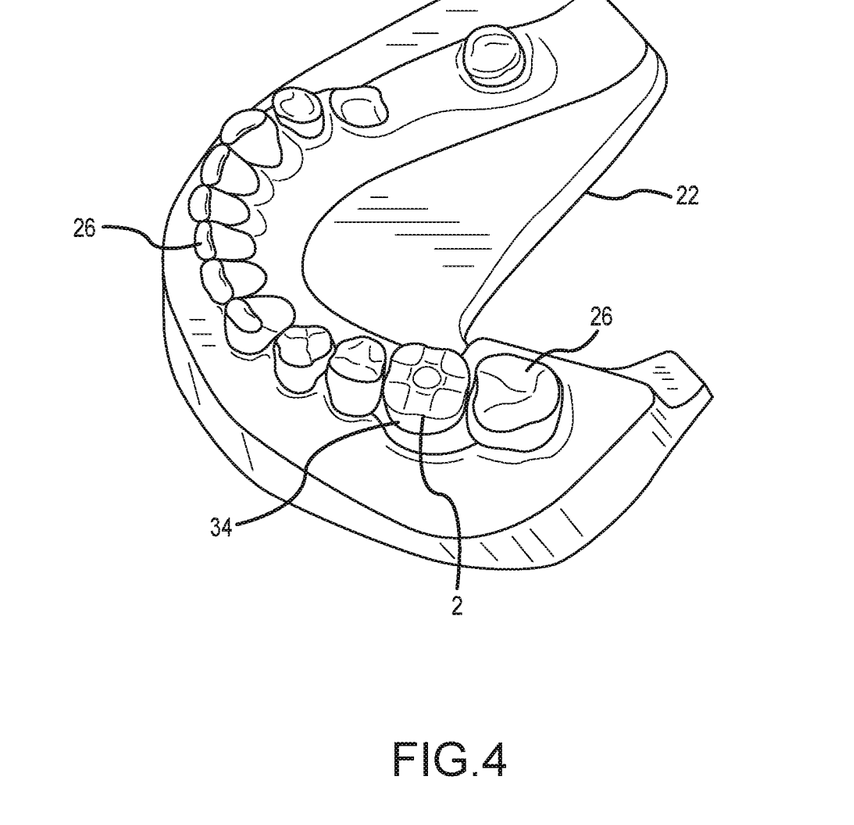
FIG. 4 is a perspective view of a dental arch cast with an interconnected provisional dental crown.

FIGS. 1 and 2 show a provisional dental crown 2 that may be used with some of the processes described herein. The provisional dental crown 2 includes a symmetrical outer surface 6 that terminates in a conical or semi-conical portion 10 designed to interface with the base of an abutment and the patient's gum line. Those of ordinary skill in the art will appreciate that the shape of the provisional dental crown need not be symmetrical and can be made to any shape to fit the dentist's or oral surgeon's needs or to fit an abutment with a non-planar collar. The provisional dental crown includes a hole 14 that allows access to screws or fasteners that interconnect the abutment to the implant to be accessed. After the provisional dental crown is in placed on the abutment, the hole 14 is filled with a cotton pellet and a dental material such as composite, resin, or temporary filling material. When the dental implant is osseo-integrated into the bone and tissue healing is complete, the provisional dental crown 2 is removed and a permanent crown is attached to the existing abutment, or a new abutment may be placed using known techniques. Embodiments of the present invention contemplate using these types of provisional dental crowns to fabricate radiographic guides or surgical guides.

FIGS. 3-7 illustrate the process of fabricating a radiographic guide 18, which may be used as a surgical guide of one embodiment of the present invention. Here, the provisional dental crown 2 is used instead of a denture tooth to fabricate the radiographic guide 18. This process omits the need to make a cast of the denture tooth with putty as done in the process described above. In operation, a dental arch cast 22 is initially made of the patient's teeth. The dental arch cast 22 will include existing tooth representations 26 and voids 30 associated with missing teeth. Next, the provisional dental crown 2, which may be the same shape as the provisional dental crown that will be placed in the patient's mouth after surgery, is affixed to the dental arch cast 22 using wax 34 (see FIG. 4).

Figure 5:
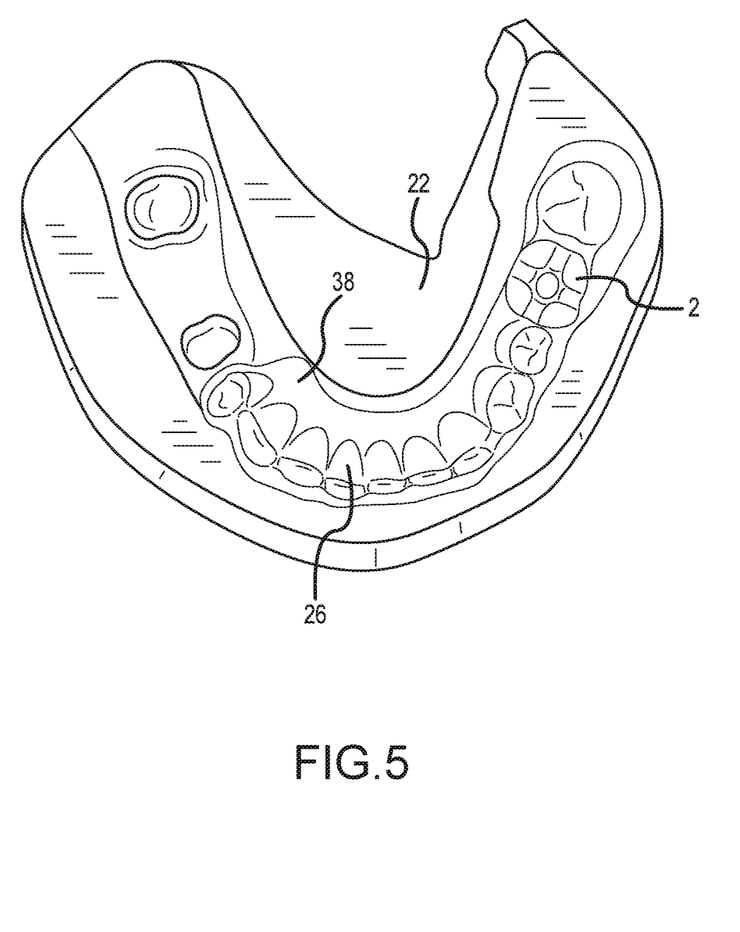
FIG. 5 is a top plan view of the dental arch cast and provisional dental crown with a layer of orthodontic acrylic resin applied thereto.

Next, as shown in FIG. 5, orthodontic acrylic resin 38, or similar material, is added over the dental arch cast 22 and is used to create an impression of the existing tooth representations 26 and the provisional dental crown 2. As one of ordinary skill in the art will appreciate, before the orthodontic acrylic resin 38 is applied to the dental arch cast 22, a separating agent is applied such that once the orthodontic acrylic resin 38 cures it can be easily removed from the dental arch cast 22. The separating agent is not added to the provisional crown so the acrylic resin will bond to the provisional crown. In other embodiments, the separating agent is applied to the provisional crown so it is not bonded to the acrylic resin. In this example, the provisional crown, or another crown of same or similar shape, is selectively interconnected to the radiographic and/or surgical guide.

Figure 6:
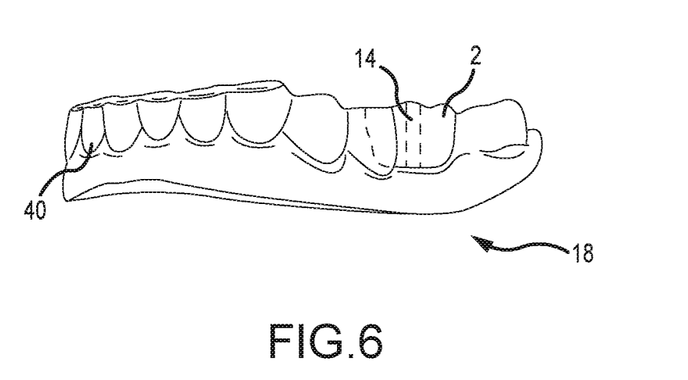
FIG. 6 is a side elevation view of a radiographic guide.
Figure 7:
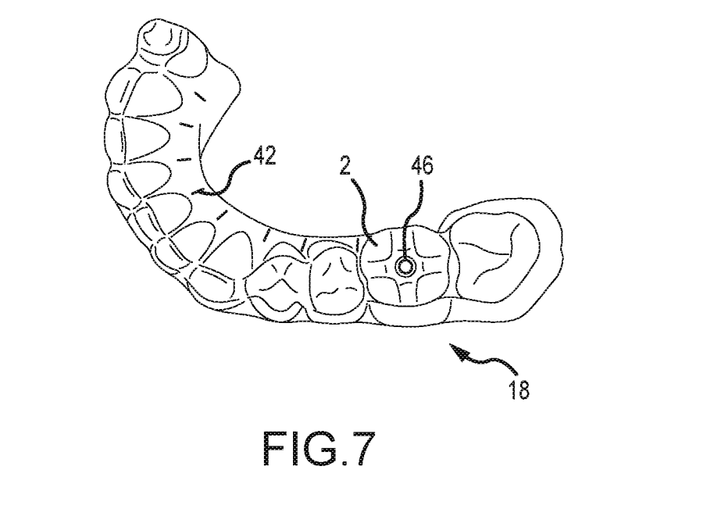
FIG. 7 is a top plan view of the radiographic guide shown in FIG. 6.

FIGS. 6 and 7 show the radiographic guide 18 of one embodiment of the present invention that is made up of the cured orthodontic acrylic resin 38 removed from the dental arch cast. The orthodontic acrylic resin 38 is bonded to the provisional dental crown 2 and, thus, includes a member that corresponds with the void in the patient's mouth associated with the extracted tooth. The radiographic guide will also include recesses 40 that receive the patient's existing teeth. A plurality of markers 42 may be added to the radiographic guide 18. Further, the hole 14 of the provisional dental crown can be filled with radio-opaque material. The hole 14 of the provisional crown directly correlates with the axis of the dental abutment and implant. Thus, by filling the hole 14 with a radio-opaque material, the radiographic images portray the exact location and angulation that the dental implant should be placed. This gives the oral surgeon information on quantity and quality of bone at the desired implant location.

In operation, the radiographic guide 18 is placed in the patient's mouth wherein the provisional dental crown 2 will seat in the void associated with the missing tooth or teeth. Various radiographic images are then taken of the patient's mouth wherein the markers 42 and radio-opaque material 46 positioned in the provisional dental crown 2 will help the dentist and oral surgeon assess the viability of placing the implant. Accordingly, instead of starting bottom-up from the bone wherein the provisional dental crown is made by traditional methods, the implant is planned top-down wherein the provisional dental crown will define the implant location. If the radiographic tests indicate the predetermined location for the implant is not ideal, the location of the present provisional dental crown and associated hole can be altered in a new radiographic guide that can be made relatively quickly. If the implant location as defined by the radiographic guide is acceptable, the radiographic guide can be used as a surgical guide wherein the hole of the provisional dental crown or an added metal guide sleeve (placed into the hole of the provisional crown) is used to guide the oral surgeon's drill.

After the implant is placed, an abutment is interconnected. The abutment will accept a provisional dental crown of the same or similar shape as that used to create a radiographic guide or surgical stent. Once the patient's gum tissues and bone have healed, the provisional dental crown is removed and a suitable permanent crown is interconnected to the same abutment or a new abutment is used.

While various embodiments of the present invention have been described in detail, it is apparent that modifications and alterations of those embodiments will occur to those skilled in the art. However, it is to be expressly understood that such modifications and alterations are within the scope and spirit of the present invention, as set forth in the following claims. Further, the invention(s) described herein is capable of other embodiments and of being practiced or of being carried out in various ways. In addition, it is to be understood that the phraseology and terminology used herein is for the purpose of description and should not be regarded as limiting. The use of "including," "comprising," or "having" and variations thereof herein is meant to encompass the items listed thereafter and equivalents thereof as well as additional items.

What is claimed is:

1. A method of fabricating a radiographic guide, comprising:
    taking an impression of a patient's dental arch;
    using the impression to create a cast of the patient's dental arch, the cast including at least one void;
    using wax to interconnect a provisional implant crown to the cast, the provisional implant crown being associated with the at least one void, wherein the provisional implant crown includes a hole with a radio-opaque material;
    applying partially-cured orthodontic acrylic resin over the cast and the provisional implant crown;
    allowing the orthodontic acrylic resin to cure, which causes the provisional implant crown to bond with the orthodontic acrylic resin;
    removing the cured orthodontic acrylic resin and interconnected provisional implant crown from the cast;
    obtaining a radiographic image of the radiographic guide positioned in the patient's mouth;
    analyzing the radiographic image to assess if the hole is positioned and aligned with an area of the patient's maxilla or jaw that is conducive for accepting and securing a dental implant;
    removing the radiographic guide from the patient's mouth;
    removing the radio-opaque material from the hole;
    creating a new hole in the provisional implant crown;
    coating the new hole with a radio-opaque material;
    placing the radiographic guide into the patient's mouth;
    obtaining a second radiographic image; and
    analyzing the second radiographic image to assess if the new hole is positioned and aligned with the area of the patient's maxilla or jaw that is conducive for accepting and securing a dental implant.

2. The method of claim 1, wherein the radio-opaque material removed from the hole comprises a coating of radio-opaque material applied to a surface of the hole.

3. The method of claim 1, further comprising adding radiographic markers to the radiographic guide.

4. The method of claim 1, further comprising adding a separating agent to the cast, but not the provisional implant crown.

5. The method of claim 1, wherein the provisional implant crown substantially matches the shape of a provisional implant crown that will be interconnected to a dental implant via an abutment.

6. The method of claim 1, wherein the hole does not extend through the provisional implant crown.

7. A method of fabricating a radiographic guide that can be used as a surgical guide, comprising:
    obtaining an impression of a patient's dental arch;
    using the impression to create a cast of the patient's dental arch, the cast including at least one void;
    associating at least one tooth representation with the at least one void, the at least one tooth representation having a hole including a radio-opaque material;
    applying orthodontic acrylic resin over the cast and the at least one tooth representation;
    curing the orthodontic acrylic resin;
    removing the cured orthodontic acrylic resin and the at least one tooth representation from the cast;
    obtaining a radiographic image of the radiographic guide positioned in the patient's mouth;
    analyzing the radiographic image to assess if the hole is positioned and aligned with an area of the patient's maxilla or jaw that is conducive for accepting and securing a dental implant;
    removing the radiographic guide from the patient's mouth;
    removing the radio-opaque material from the hole;
    creating a new hole in the at least one tooth representation;
    coating the new hole with a radio-opaque material;
    placing the radiographic guide into the patient's mouth;
    obtaining a second radiographic image of the radiographic guide; and
    analyzing the second radiographic image to assess if the new hole is positioned and aligned with the area of the patient's maxilla or jaw that is conducive for accepting and securing a dental implant.

8. The method of claim 7, wherein the at least one tooth representation is a provisional implant crown that substantially matches the shape of a provisional implant crown that will be interconnected to a dental implant via an abutment.

9. The method of claim 7, wherein the at least one tooth representation is bonded to the cured orthodontic resin.

10. The method of claim 7, wherein the at least one tooth representation is selectively interconnected to the cured orthodontic resin.

11. The method of claim 7, wherein the hole does not extend through the at least one tooth representation.

12. The method of claim 7, further comprising at least one of coating the hole with a radio-opaque material, and adding radiographic markers to the radiographic guide.

13. The method of claim 7, further comprising adding a separating agent to the cast.

14. The method of claim 13, wherein the separating agent is not added to the at least one tooth representation.

15. A method of placing a provisional implant crown into a patient's maxilla or jaw, comprising:
    obtaining an impression of a patient's dental arch;
    using the impression to create a cast of the patient's dental arch, the cast including a void that corresponds with an extracted tooth;
    associating a tooth representation with void, the tooth representation having a hole;
    applying orthodontic acrylic resin over the cast and the tooth representation;
    curing the orthodontic acrylic resin;

removing the cured orthodontic acrylic resin and the tooth representation from the cast, the cured orthodontic acrylic resin and the tooth representation defining a radiographic guide;

placing the radiographic guide into the patient's mouth wherein the tooth representation is associated with the site of the extracted tooth;

obtaining a radiographic image of the radiographic guide;

analyzing the image to assess if the hole is positioned and aligned with an area of the patient's maxilla or jaw that is conducive for accepting and securing a dental implant;

using the radiographic guide as a surgical guide, wherein the hole is used to guide surgical tools that prepare the patient's maxilla or jaw for receipt of an implant;

interconnecting the implant to the patient's maxilla or jaw;

interconnecting an abutment to the implant; and interconnecting the provisional implant crown to the abutment.

16. The method of claim 15, wherein the tooth representation has a shape substantially similar to that of the provisional implant crown.

17. The method of claim 15, wherein if after analyzing the image, the proposed implant placement is not ideal, removing the radiographic guide from the patient's mouth, removing a radio-opaque material from the hole, creating a new hole in the tooth representation, coating the new hole with a radio-opaque material, placing the radiographic guide into the patient's mouth, obtaining a second radiographic image of the radiographic guide, and analyzing the second image to assess if the new hole is positioned and aligned with the area of the patient's maxilla or jaw that is conducive for accepting and securing a dental implant.

18. The method of claim 15, further comprising at least one of coating the hole with a radio-opaque material, and adding radiographic markers to the radiographic guide.

* * * * *